United States Patent [19]

Grundy et al.

[11] Patent Number: 5,567,582
[45] Date of Patent: Oct. 22, 1996

[54] VARIANTS OF CYTOMEGALOVIRUS GB

[75] Inventors: Jane Grundy; Vincent Emery, both of London, England

[73] Assignee: Royal Free Hospital School of Medicine, London, England

[21] Appl. No.: 197,811

[22] Filed: Feb. 17, 1994

Related U.S. Application Data

[63] Continuation of Ser. No. 946,472, filed as PCT/GB91/00574, Apr. 11, 1991, abandoned.

[30] Foreign Application Priority Data

Apr. 11, 1990 [GB] United Kingdom .................. 9008223

[51] Int. Cl.$^6$ .............................. C12Q 1/70; C12P 19/34; C07H 21/04
[52] U.S. Cl. ......................... 435/5; 435/91.2; 536/24.33; 935/77; 935/78
[58] Field of Search .................... 435/5, 91.2; 536/24.33

[56] References Cited

FOREIGN PATENT DOCUMENTS

| 0257754 | 3/1988 | European Pat. Off. |
| WO89/07143 | 8/1989 | WIPO |
| WO90/11302 | 10/1990 | WIPO |

OTHER PUBLICATIONS

7th International Congress of Immunology, Jul. 30–Aug. 5, 1989, West Berlin, Abstracts.
Chemical Abstracts, vol. 106, 1987, p. 156, "Structure and expression of the herpes simplex virus . . ." Stuve et al.
10–Microbial Biochem, vol. 110, 1989, p. 403, "Identification of a neutralizing epitope on glycoprotein . . ." Utz et al. Abstract.
10107 Journal of General Virology, Apr. 1989, "A Major Neutralizing Domain Maps within the Carboxyl–terminal . . ." Banks et al.

Current Topics in Microbiology & Immun. vol. 154, 1990 pp. 126–168 "Analysis of the Protein–Coding Content . . ." Chee et al.
DNA, vol. 4, No. 2, 1985, "Supercoil Sequencing: A Fast and Simple Method for Sequencing . . ." Chen et al pp. 165–170.
The EMBO Journal, vol. 5, No. 11, pp. 3057–3063, 1986, "Identification of the human . . ." Cranage et al.
Journal of Virology, Apr. 1988, pp. 1416–1422, "Identification and Expression of a Human . . ." Cranage et al.
J. gen. Virol, 1987, 68, pp. 793–803, "$\beta_2$ Microglobulin Enhances the Infectivity . . ." Grundy et al.
Proc. Natl. Acad. Sci. USA, vol. 81, pp. 876–880, Feb. 1984, "Murine monoclonal antibody to a single . . ." Rasmussen et al.
"Primer–Directed Enzymatic Amplification of DNA with a . . ." Jan. 1988 Saiki et al., pp. 487–491.
Demmler et al., (1988) J. Infect. Dis. 158 (6): 1177–1184.
Shibata et al. (1988) J. Infect. Dis. 158 (6): 1105–1192.
Roy et al, J. Gen. Virol. 74:1–6 (1993).
Sequence variation within neutralizing Epitopes . . . Wagner et al, J. Virol. 66(9): 5290 (1992).

*Primary Examiner*—Stephanie W. Zitomer
*Attorney, Agent, or Firm*—Nixon & Vanderhye PC

[57] ABSTRACT

The present invention relates to a process for detecting DNA, or a fragment thereof, that includes at least one sequence variation in relation to the sequence of a genomic region of a CMV strain that corresponds to the gB gene, with the proviso that the variation is not that found in the Towne strain of CMV, and that a CMV genome having the sequence variation would be capable of reproduction in a host system which supports reproduction of wild type CMV. The invention further relates to primers suitable for use in such a process.

2 Claims, 1 Drawing Sheet

Fig.1.

HIND III RESTRICTION MAPS OF STRAINS AD169 (A), DAVIS (D), AND TOWNE (T) AND 28 CLINICAL ISOLATES OF HUMAN CYTOMEGALOVIRUS.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 366 base pairs
        ( B ) TYPE: nucleic acid
        ( C ) STRANDEDNESS: double
        ( D ) TOPOLOGY: unknown ( i i ) MOLECULE TYPE: DNA (genomic)

( i i i ) HYPOTHETICAL: NO ( i v ) ANTI-SENSE: NO ( v i ) ORIGINAL SOURCE:
        ( B ) STRAIN: AD169

( i x ) FEATURE:
        ( A ) NAME/KEY: CDS
        ( B ) LOCATION: 1..366

( x i ) SEQUENCE DESCRIPTION: SEQ ID NO:1:

```
AAG GTG CTG CGT GAT ATG AAC GTG AAG GAA TCG CCA GGA CGC TGC TAC      48
Lys Val Leu Arg Asp Met Asn Val Lys Glu Ser Pro Gly Arg Cys Tyr
 1               5                  10                  15

TCA CGA CCC GTG GTC ATC TTT AAT TTC GCC AAC AGC TCG TAC GTG CAG      96
Ser Arg Pro Val Val Ile Phe Asn Phe Ala Asn Ser Ser Tyr Val Gln
                20                  25                  30

TAC GGT CAA CTG GGC GAG GAC AAC GAA ATC CTG TTG GGC AAC CAC CGC     144
Tyr Gly Gln Leu Gly Glu Asp Asn Glu Ile Leu Leu Gly Asn His Arg
            35                  40                  45

ACT GAG GAA TGT CAG CTT CCC AGC CTC AAG ATC TTC ATC GCC GGG AAC     192
Thr Glu Glu Cys Gln Leu Pro Ser Leu Lys Ile Phe Ile Ala Gly Asn
        50                  55                  60

TCG GCC TAC GAG TAC GTG GAC TAC CTC TTC AAA CGC ATG ATT GAC CTC     240
Ser Ala Tyr Glu Tyr Val Asp Tyr Leu Phe Lys Arg Met Ile Asp Leu
 65                 70                  75                  80

AGC AGT ATC TCC ACC GTC GAC AGC ATG ATC GCC CTG GAT ATC GAC CCG     288
Ser Ser Ile Ser Thr Val Asp Ser Met Ile Ala Leu Asp Ile Asp Pro
                85                  90                  95

CTG GAA AAC ACC GAC TTC AGG GTA CTG GAA CTT TAC TCG CAG AAA GAG     336
Leu Glu Asn Thr Asp Phe Arg Val Leu Glu Leu Tyr Ser Gln Lys Glu
               100                 105                 110

CTG CGT TCC AGC AAC GTT TTT GAC CTC GAA                             366
Leu Arg Ser Ser Asn Val Phe Asp Leu Glu
           115                 120
```

( 2 ) INFORMATION FOR SEQ ID NO:2:

( i ) SEQUENCE CHARACTERISTICS:
        ( A ) LENGTH: 122 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Lys Val Leu Arg Asp Met Asn Val Lys Glu Ser Pro Gly Arg Cys Tyr
 1               5                  10                  15

Ser Arg Pro Val Val Ile Phe Asn Phe Ala Asn Ser Ser Tyr Val Gln
                20                  25                  30
```

```
Tyr Gly Gln Leu Gly Glu Asp Asn Glu Ile Leu Leu Gly Asn His Arg
        35                  40                      45

Thr Glu Glu Cys Gln Leu Pro Ser Leu Lys Ile Phe Ile Ala Gly Asn
        50              55                  60

Ser Ala Tyr Glu Tyr Val Asp Tyr Leu Phe Lys Arg Met Ile Asp Leu
65                  70                  75                      80

Ser Ser Ile Ser Thr Val Asp Ser Met Ile Ala Leu Asp Ile Asp Pro
                85                  90                  95

Leu Glu Asn Thr Asp Phe Arg Val Leu Glu Leu Tyr Ser Gln Lys Glu
            100             105                 110

Leu Arg Ser Ser Asn Val Phe Asp Leu Glu
        115             120
```

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( B ) STRAIN:

( i x ) FEATURE:
        ( A ) NAME/KEY: CDS
        ( B ) LOCATION: 1..25

( x ) SEQUENCE DESCRIPTION: SEQ ID NO:3:

GAGGACAACG AAATCCTGTT GGGCA        25

( 2 ) INFORMATION FOR SEQ ID NO:4:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( B ) STRAIN:

( i x ) FEATURE:
        ( A ) NAME/KEY: CDS
        ( B ) LOCATION: 1..366

( x ) SEQUENCE DESCRIPTION: SEQ ID NO:4:

GTCGACGGTG GAGATACTGC TGAGG        25

VARIANTS OF CYTOMEGALOVIRUS GB

This is a continuation of application Ser. No. 07/946,472, filed as PCT/GB91/00574, Apr. 11, 1991, now abandoned.

This invention relates to the detection of viruses or virus antibodies and is particularly concerned with the detection of viruses of the Herpes group, the production and detection of antibodies to such viruses, and to vaccines against these viruses.

The Herpes group of viruses are a group of considerable clinical significance, the most important members of the group being Herpes Simplex (HSV), Cytomegalovirus (CMV), Epstein Barr virus (EBV) and Varicella-zoster virus (VZV). Infections with CMV occur frequently in the United Kingdom so that 60% of adults have evidence of past infection. Occasionally, the virus produces cases of Paul Bunnell negative glandular fever but the vast majority of infected people remain entirely asymptomatic. This virus infection is therefore primarily of medical importance in specific groups of patients which are neonates with congenital infection, and immuno-compromised individuals, such as recipients of renal or bone marrow allografts or patients with the acquired immunodeficiency syndrome (AIDS). In each of these groups of patients, CMV is an important pathogen and it would be very desirable, from the clinical point of view, to have available an assay method that can reliably identify the presence of CMV in clinical samples.

The DNA sequence of the entire CMV genome has now been determined (Chee et al, 1989). The virus has 54 reading frames characteristic of glycoprotein genes or exons of glycoprotein genes. It is not however known how many of these potential glycoproteins are actually translated in the infected cell, expressed on the infective cell surface, or actually incorporated into the virus particle. Two CMV glycoproteins, named gB (Cranage et al 1986) and gH (Cranage et al 1988), have been well studied, and have been shown to be present on the vital envelope. They have both been shown to be recognised by neutralising murine monoclonal antibodies (Utz et al 1989, Rasmussen et al 1984), suggesting that these proteins are important for the infectivity of the virus and are thus potential candidates for a subunit CMV vaccine.

The majority of neutralising murine monoclonal antibodies raised against CMV recognise gB rather than gH (Gompels et al 1988), suggesting that in the mouse at least gB is more immunogenic than gH. The neutralising epitope recognised by one gB-specific antibody, 7–17, which neutralises CMV in vitro has recently been determined (Utz et al 1989). Using overlapping fragments of the open reading frame for gB from the laboratory strain AD169 expressed as β-galactosidase fusion proteins in E.Coli, the antibody was shown to recognise a linear sequence between amino acid residues 609 and 626. Liu et al (1989) used overlapping synthetic hexapeptides from the gB sequence of the Towne laboratory strain and identified two other linear neutralising epitopes, mapping to residues 559–567 and 589–594. Banks et al (1989), using the Towne strain of CMV, identified at least two epitopes of gB which may be neutralised by murine monoclonal antibodies. These two epitopes occur between residues 620–680. Therefore, in addition to the two sites described by Liu et al and the one described by Utz et al, there is at least one further neutralising epitope recognised by murine monoclonal antibodies to the gB molecule.

Sequence Seq ID No. 1 shows the DNA and peptide sequence of a region of the laboratory strain AD169. This region is part of the gB gene. The numbering to the DNA follows conventional usage, e.g. as described in EP-A-236 145. Sequence ID No. 2 shows the translation of the open reading frame of Seq ID No. 1. The numbering follows the same usage as ID No. 1.

FIG. 1 shows an analysis of Hind III digests of CMV DNA from 3 laboratory samples and 28 clinical isolates of CMV.

The epitopes of the gB molecule described above are of particular importance in the laboratory for both biological studies and clinical purposes. Antibodies to these epitopes, such as the antibody 7–17, are of use as diagnostic agents. In addition, because CMV can establish latency and is also potentially oncogenic, ethical considerations preclude the use of a live attenuated CMV vaccine. Therefore, potential CMV vaccines will probably be based on important viral proteins rather than attenuated virus.

A vaccine against CMV based on one or more epitopes of gB will only be effective against wild-type strains of CMV encountered in clinical practice if the corresponding epitopes of the laboratory strains upon which the vaccines are based correspond to the clinical strains. Similarly, antibodies raised against laboratory strains will only detect clinical isolates of CMV which include epitopes closely similar, if not identical, to those against which the antibodies were raised. Clearly, differences between laboratory and clinical strains could result in vaccines against CMV which are ineffective, or diagnostic antibodies which give false negatives.

We have now isolated and analyzed clinical CMV samples by restriction enzyme digestion with Hind III. FIG. 1 shows such an analysis for 28 CMV strains found in the clinic (1–28) and a comparison with 3 tissue culture strains, AD169(A) Towne(T) and Davis(D). Although each isolate has a unique Hind III restriction profile, each profile contains polymorphisms which appear to segregate with aspects of the three laboratory adapted strains. For example, fragment J of AD169 contains an additional Hind III site in the Towne and Davis and strains and this feature is also shared by clinical samples 9–12 and 28. In all, some specific polymorphisms may occur more frequently within the wild type population implying that only certain strains of virus are replication competent and that these are the species observed following culture of clinical specimens.

Global restriction analysis of the type described above does not however provide any information on the functional significance of sequence heterogeneities. There may also be sequence heterogeneities within large scale polymorphic fragments which will not be identified by this analysis. Thus, although restriction enzyme analysis of the gB region may indicate similarity between laboratory and clinical strains, no information concerning specific sequence variation can be deduced. For instance, it can not be determined whether the variation in restriction sites occurs in important epitopes or outside such regions.

We have now surprisingly found that there is DNA sequence variation, some of which results in amino acid variation, in the gB coding region of clinical isolates of CMV. This includes sequence variation in the epitope recognised by the antibody 7–17.

Although CMV may be analyzed by any suitable means known in the art, the size of the CMV virus, at 235 kb being the largest viral genome known to infect man, precludes some techniques from being of use when the variation in a large number of samples is to be analyzed. We have used the polymerase chain reaction (PCR; Saiki et al 1988) to amplify a 100 nucleotide fragment from the gB gene that encompasses a neutralising epitope of interest of each clinical CMV isolate. The amplified DNA is then cloned into suitable plasmid vectors and the DNA sequence of at least 3 individual clones of each isolate determined. The particular results obtained are presented in the examples which follows.

Although many of the DNA substitutions identified result in no change to the amino acid sequence, certain changes do result in alterations to the previously determined amino acid sequence of gB. In particular, amino acid residue number 612, leucine, has been identified as a residue which may be substituted. More specifically, this residue may be replaced by His, Val or Phe. Residue number 622, asparagine, may also be substituted. In particular, it may be replaced by tyrosine. Residue number 645, aspartic acid may also be substituted. In particular, it may be replaced by glycine.

Changes to the amino acid sequence of neutralising epitopes are especially significant, since this may result in the failure of an antibody to the unaltered epitope to recognise the changed epitope. Likewise, if a clinical sample is being analyzed for the presence of antibodies to an epitope of CMV via the use of peptides comprising an unaltered peptide sequence, such antibodies may not be detected if they have been produced against an altered epitope.

In the clinical situation, this may result in false negatives when samples are being analyzed for the presence of CMV. The present invention thus provides:

DNA of the sequence ID No. 1 which includes at least one variation, for example 1, 2, 3 or 4 to 10 variations, which is a substitution, insertion or deletion, but which otherwise retains the character of CMV, and fragments thereof;

preferred variation being one or more, for example 2, 3, or 4 to 10, substitutions, at least one of which results in the alteration of the translation of the DNA;

particularly preferred DNA fragments of the type described above being those corresponding to nucleotides 1831–1857, 1921–1938, 1981–2034, 2068–2115 and fragments thereof;

recombinant vectors, eg plasmids, phage or virus, carrying such DNAs, and optionally containing sequences for the selection of the said vectors and/or signals for the expression of the DNA; and cells, eg bacterial, yeast, insect or mammalian, transfected or transformed with the above vectors.

The DNA sequences of the invention will preferably be at least 80%, eg 90, 95 or 99% homologous to a region of corresponding length of the sequence ID No 1.

Particular substitutions which are preferred are shown in Table 1 as sequences 1–27.

The DNA sequence of ID No. 1 and where appropriate fragments thereof, consisting of the following substitutions found in the Towne strain of DCV:
1854 C to T,
1897 C to A,
1947 C to T,
2019 G to C,
2076 T to C,
2106 G to A,
2109 T to C,
2127 T to C,
2166 G to A,
2167 C to T,
2190 C to T and
2196 A To G
is excluded from the invention.

The invention also provides polypeptides of the sequence of ID No. 2 which include at least one variation for example 1, 2, 3 or 4 to 10 variations which is a substitution, insertion or deletion, but which otherwise retains the character of CMV. Peptides of this type corresponding to residues 559–567, 589–594, 609–626, 638–653 and fragments thereof are preferred, and the peptide 609–626 and fragments thereof is especially preferred.

Of the peptides of the invention which correspond to residues 609–626 and fragments thereof, those with substitutions at residues 612 or 622 (when they are present) are particularly preferred. More precisely, the following substitutions are especially preferred:

| | |
|---|---|
| 612 | Leu—His |
| 612 | Leu—Val |
| 612 | Leu—Phe |
| 622 | Asn—Tyr |
| 645 | Asp—Gly. |

The substitution at 622 may occur alone or in combination with each other or with any of the substitutions at 612, eg 612 Leu-His.

The peptide sequences of the invention will preferably be at least 80%, e.g. 85% or 90% homologous to a region of corresponding length of sequence ID No. 2.

The peptides may be produced by synthetic means known in the art of peptide chemistry or by recombinant means, eg using an expression vector of the type described hereinbefore.

The term "retains the character of CMV", means that when a DNA (or peptide) sequence of the invention is included in a gB gene (or protein) which in turn forms part of a CMV genome, the CMV genome will be capable of reproduction in a host system in a manner substantially similar to wild-type CMV strains. Thus a CMV virus which comprises a DNA (or peptide) sequence of the present invention will be able to produce proteins essential for its reproduction in a host cell, and also produce other proteins capable of associating with each other for the formation of virus particles.

The invention further provides antibodies to the peptides of the invention. The antibodies may be polyclonal or monoclonal.

Polyclonal antibodies may be produced by conventional means, eg injecting a host animal eg a rat or rabbit with a peptide of the invention, optionally linked to a carrier, and recovering immune serum.

Monoclonal antibodies may also be produced by conventional methods, eg following the above procedure for the preparation of polyclonal antibodies but sacrificing the host animal and fusing its spleen cells with an immortalizing cell line, eg a mouse myeloma cell line.

Antibodies according to the invention may be whole antibodies or binding fragments thereof, i.e. fragments which retain the ability to bind to antigen to which it was raised. Antibodies also include altered antibodies, eg. humanized antibodies as described in EP-A-0125023 (Genentech), or chimeric antibodies as described in EP-A-0239400 (Winter).

The invention further provides a kit for the detection of the presence of a CMV virus strain or antibodies against the strain in a sample, eg the serum of a patient, which comprises a peptide of the invention or an antibody thereto of the type described above, the said peptide or antibody being optionally immobilized and/or labelled, eg with an enzyme, fluorescent marker or radiolabel.

The CMV virus may be detected in a sample by using the above peptides as a binding agent to look for the presence or absence of antibodies, or by using antibodies of the invention as described above to look for the presence or absence of CMV viral proteins.

The invention further provides a vaccine for the treatment or prophylaxis of CMV virus infections which comprises a peptide or an antibody of the type described above in association with a pharmaceutically acceptable carrier or diluent. A peptide vaccine may be administered as free peptide, peptide attached to a carrier molecule, or form part of a recombinant epitope of a clinically acceptable carrier virus, e.g. vaccinia virus.

The following example illustrates the invention.

EXAMPLE 1

Patients undergoing renal or bone marrow transplantation at the Royal Free Hospital have surveillance cultures of urine, saliva and blood collected weekly. Clinical specimens were tested for the presence of CMV and were simultaneously inoculated onto primary Human embryo lung fibroblasts for CMV culture.

Clinical isolates of HCMV were propagated for 1–2 passages in primary human embryo lung fibroblasts. Viral DNA was isolated as follows: after discarding culture supernatants, Lysis buffer (0.1M Tris -HCl pH 7.5, 0.001M EDTA, 0.5% SDS) was added to the cells and chromosomal DNA was removed from the lysates by overnight precipitation with NaCl (5M; 0.25 volumes) at 4° C. Following centrifugation at 20,000 g for 30 minutes at 4° C., supernatants containing viral DNA were collected. Viral DNA was purified by treatment with proteinase K (200 μg/ml) followed by phenol/chloroform extraction and finally precipitation with ethanol.

DNA derived from each clinical isolate of HCMV was digested with Hind III and the resulting DNA fragments resolved by electrophoresis through a 0.7% agarose gel. DNA fragments were transferred to nylon filters (Hybond N, Amersham International) and probed using $^{32}P$ labelled cloned Hind III restriction fragments derived from the unique long and unique short regions of the HCMV AD169 genome using a random priming kit (Amersham International) and established methodologies (Sambrook et al, 1989).

PCR amplification was performed essentially as described by Saiki and coworkers (1986). The primers used for the PCR amplification were as follows:

Primer 1: 5'-GAGGACAACGAAATCCTGTTGGGCA (SEQ ID NO:3)

Primer 2: 5'-GTCGACGGTGGAGATACTGCTGAGG (SEQ ID NO:4)

The reaction mixture contained the following components: CMV DNA (100 ng), 25 mM Tris-HCl pH 8.9, 17 mM ammonium sulphate, 3 mM magnesium chloride, 10 mM 2-mercaptoethanol, 0.002% gelatin, 1 μM of 5'-phosphorylated (Sambrook et al, 1990) HCMV specific primers, 200 μM of each of the deoxynucleotides (dATP, dCTP, dGTP, dTTP and 1 unit of Taq polymerase (Amplitaq, Perkin Elmer-Cetus) in a total volume of 100 ul. The reaction mixture was overlaid with 100 ul of mineral oil and the samples denatured by heating to 95° C. for 6 minutes and then amplified by 35 PCR cycles using a Hybaid thermal reactor (HBTR1). One cycle involved denaturation at 94° C. for 90 seconds, primer annealing at 60° C. for 90 seconds and extension at 72° C. for 120 seconds. After the final cycle the samples were incubated at 72° C. for a further 10 minutes.

Amplified products (100 base pairs) were analysed on a 1.6% agarose gel containing ethidium bromide and their authenticity confirmed by Souther blotting and hybridisation with a $^{32}P$-labelled AD169 Hind III F probe.

The 100 base pair PCR amplified products were treated with the Klenow fragment of DNA polymerase I (Amersham) in the presence of deoxynucleotide triphosphates (2.5 mM) to create blunt ended fragments then 5' phosphorylated with polynucleotide kinase and ATP as described by Sambrook et al (1989). The resulting fragments were ligated into Sma I cut dephosphorylated pT7T3/18U (Pharmacia). Following transformation of competent E.coli JM 109, clones containing the fragment were identified by colony hybridisation using a $^{32}P$-labelled AD169 Hind III F probe (Sambrook et al, 1989).

The clones were sequenced on both strands according to the plasmid sequencing protocols developed by Chen and Seeburg (1985). At least three clones were sequenced on both strands for PCR products derived from the CMV clinical isolate to confirm the fidelity of the PCR reaction.

Table 1 shows the variation detected in these isolates. The numbering used corresponds to the attached sequence listings.

The amino acid sequence for the amplified region was determined from the DNA sequence by means of the triplet codon designations.

| Variant No | Sequence Changes | Coding Changes |
|---|---|---|
| 1 | 1991 T—A | 612 Leu—His |
|   | 2020 A—T | 622 Asn—Tyr |
| 2 | 1990 C—G | 612 Leu—Val |
|   | 2031 C—T | — |
|   | 2034 G—A | — |
|   | 2037 C—T | — |
| 3 | 2019 G—C | — |
| 4 | 2019 G—C | — |
| 5 | 1990 C—T | 612 Leu—Phe |
|   | 2031 C—T | — |
|   | 2034 G—A | — |
|   | 2037 C—T | — |
| 6 | 2019 G—C | — |
| 7 | 2019 G—C | — |
| Isolate No | Sequence Changes | Coding Changes |
| 8 | 2019 G—C | — |
| 9 | 2019 G—C | — |
| 10 | 2019 G—C | — |
| 11 | 2019 G—C | — |
| 12 | 1977 T—C | — |
|   | 2019 G—C | — |
| 13 | 2090 A—G | 645 Asp—Gly |
| 14 | 2088 C—G | — |
|   | 2090 A—G | 645 Asp—Gly |

REFERENCES

Banks T, et al (1989). J Gen Virol 70:979–985.
Chee M S, et al (1989). Curr Top Imm Microbiol In Press.
Chen E Y and Seeburg P H (1985). DNA 4, 165–170.
Cranage M P, et al (1986). EMBO J 5:3057–63
Cranage M P, et al (1988). J Virol 62:1416–1422.
Gompels U A, et al (1987). J Gen Virol 68:793–803.
Liu N-YC, et al (1989). Presentation at the 7th International Congress of Immunology, Berlin 1989, Abstract Number 98-59.
Rasmussen L E, et al (1984). Proc Natl Acad Sci 79:616–620
Saiki R K, et al (1988). Science 239,487–491
Sambrook J. Fritsch E F and Maniatis T (1989) Molecular Cloning: A Laboratory Manual 2nd Edition, Coldspring Harbor Laboratory Press, Coldspring Harbor, N.Y.
Utz U, et al (1989). J Virol 63:1995–2001.

We claim:

1. An oligonucleotide having the sequence

5'-GAGGACAACGAAATCCTGTTGGGCA (SEQ ID NO:3) or

5'-GTCGACGGTGGAGATACTGCTGAGG(SEQ ID NO:4).

2. A process for detecting cytomegalovirus (CMV) DNA having the sequence of SEQ ID NO:1, or a fragment of said DNA, which DNA or fragment includes at least one sequence variation in relation to the sequence of SEQ ID NO:1, with the proviso that the variation is not that found in the Towne strain of CMV, and that a CMV genome having said sequence variation would be capable of reproduction in a host system which supports reproduction of wild type CMV, which process comprises:

conducting a polymerase chain reaction on a sample suspected of containing said CMV DNA or fragment wherein the primers used in the polymerase chain reaction are:

Primer 1 5'-GAGGACAACGAAATCCTGTTGGGCA (SEQ ID NO:3)

Primer 2 5'-GTCGACGGTGGAGATACTGCTGAGG (SEQ ID NO:4), and detecting an amplification product of said polymerase chain reaction thereby detecting said cytomegalovirus DNA.

* * * * *